United States Patent [19]

Kanshin et al.

[11] Patent Number: 4,964,863
[45] Date of Patent: Oct. 23, 1990

[54] DEVICE FOR ESTABLISHING ESOPHAGOENTEROSTOMIES

[75] Inventors: Nikolai N. Kanshin; Viktor A. Lipatov; Igor A. Guskov, all of Moscow, U.S.S.R.

[73] Assignee: Moskovsky Gorodskoi Nauchno-Issledovatelsky Institut Skoroi Pomoschi Imeni N.V. Sklifosovskogo, Moscow, U.S.S.R.

[21] Appl. No.: 328,032

[22] PCT Filed: May 26, 1988

[86] PCT No.: PCT/SU88/00125
§ 371 Date: Feb. 9, 1989
§ 102(e) Date: Feb. 9, 1989

[87] PCT Pub. No.: WO88/09644
PCT Pub. Date: Dec. 15, 1988

[30] Foreign Application Priority Data

Jun. 10, 1987 [SU] U.S.S.R. ............................. 4303545

[51] Int. Cl.⁵ .............................................. A63B 17/00
[52] U.S. Cl. ................................... 606/153; 128/898
[58] Field of Search ............ 606/153; 128/898, 334 R

[56] References Cited

U.S. PATENT DOCUMENTS 4,476,863 10/1984 Kanshin et al. ..................... 606/153
4,567,891 2/1986 Kanshin et al. ..................... 606/153

FOREIGN PATENT DOCUMENTS 0995765 2/1983 U.S.S.R. .............................. 606/153
1404065 6/1988 U.S.S.R. .............................. 606/153

Primary Examiner—Randall L. Green
Assistant Examiner—Gary Jackson
Attorney, Agent, or Firm—Fleit, Jacobson, Cohn, Price, Holman & Stern

[57] ABSTRACT

The device for establishing anastomoses comprises a hollow housing (1), telescopically interconnected an outer sleeve (2) and an inner sleeve (3), both of said sleeves communicating with the hollow housing (1) through respective openings (4, 5) in their bottoms, an elastic ring (6) situated on the portion of the outside surface of the inner sleeve (3) that extends from the outer sleeve 2, a first bushing (7) having two annular grooves (11, 12) for anastomosis formation and adapted for one organ (9) being anastomosed to be fixed on said bushing, a second bushing (8) having an annular groove (13) for securing there on the other organ (10) being anastomosed, and a probe (14) passing through the interior spaces of the bushings (7, 8), the sleeves (2, 3) and the housing (1) and having a shoulder (16) for the first bushing (7) to rest upon.

3 Claims, 2 Drawing Sheets

DEVICE FOR ESTABLISHING ESOPHAGOENTEROSTOMIES

TECHNICAL FIELD

This invention relates to devices for establishing communication between tubular organs of human body and is particularly concerned with devices of establishing esophagoenterostomies.

PRIOR ART

Known in the art are suturing instruments for establishing entero- and colostomies which provide for application of a staple suture. However, such instruments fail to provide the required tightness of the applied suture which is especially necessary in surgery on the intestinal tract. Besides, the suture applied is neither adequately hemostatic nor aseptic.

One state-of-the-art device for joining tubular organs in known to comprise telescopically interconnected an outer cylindrical sleeve and an inner cylindrical sleeve having axial openings in the bottoms, and elastic ring located on the outside surface of the inner sleeve. The outer sleeve is provided with a coaxial tubular handle which is in fact a hollow housing communicating with the opening in the bottom of the outer sleeve. The device comprises also a probe and a bushing with an annular groove (SU, A, 1,158,176).

The inner sleeve is extended from the outer one so as to form an area whereon the elastic ring is located before the anastomosing procedure.

In the course of anastomosis formation the tissues to be joined are arranged on the circular groove of the bushing and are compressed by the elastic ring. The probe made as a hollow tube is passed through the interior spaces of all the elements. One of the organs being anastomosed is made fast on the probe using a purse-string, while the other organ, that is, an intestine encompasses the sleeves.

However, when the nonfixed intestine is made to plunge into the interior of the inner sleeve the tissue folds placed between the bottom of the inner sleeve and the bushing are different in thickness due to arbitrary sinking of the intestine into the inner sleeve and a possible displacement of the purse-string suture, which results in a dissimilar position of the bushing with respect to the inner sleeve so that when the elastic ring is thrown off it fails to get in between the bushing shoulders at all times but might rest upon the bushing shoulder, with the result that no suture is formed whatever. Permanent presence of the probe in the bushing till rejection of the necrosed constricted intestinal and esophageal tissues causes congestion of infected contents in the esophageal cavity, which is fraught with a danger of regurgitation of said contents into the respiratory tracts. This in turn may lead to grave complications within the postoperative period.

DISCLOSURE OF THE INVENTION

The principal object of this invention is to provide a device for establishing esophagoenterostomies, which would ensure mutual orientation of an elastic ring and a bushing in the course of anastomosis formation due to a modified construction of the anastomosis formation unit as a whole.

The aforesaid problem is accomplished due to the fact that a device for establishing esophagoenterostomies, comprising a hollow housing, an outer sleeve and an inner sleeve telescopically interconnected and communicating with the hollow housing, the inner sleeve being extended from the outer one to form an area adapted to receive an elastic ring which compresses the biological tissues being joined together, each of said sleeves having an opening in the bottom thereof, through which the respective sleeve communicates with the hollow housing, a bushing accommodated in one of the organs to be anastomosed and having a first annular groove on its outside surface for anastomosis formation by means of the elastic ring, and a probe connected to the bushing and passing through the interior spaces of the bushing, sleeves and hollow housing, according to the invention, the device incorporates a second bushing having an annular groove on its outside surface for securing thereon, with a purse-string suture, the end of the other organ of the esophagointestinal tract being anastomosed, while the first bushing has a second annular groove on its outside surface for securing, with a purse-string suture, the end of the first organ being anastomosed, said first bushing resting upon a shoulder made in the probe, which makes it possible, when establishing an anstomosis, to joint the bushings together into a single unit, to put them inside the sleeves and, while moving the inner sleeve, to throw the elastic ring off from the outside surface of the inner sleeve in order to compress the organs being anastomosed in the first annular groove of the first bushing, all the motions mentioned above being actuated by virtue of the probe travel.

It is expedient that the probe portion accommodated inside the first and second bushings has a diameter comparable with the inside diameters of said bushings.

It is also expedient that the hollow housing be provided with an adjustable stop adapted to fix the inner sleeve in position before anastomosis formation.

SUMMARY OF THE DRAWINGS

Further objects and advantages of the present invention will become evident hereinbelow by a consideration of a detailed description of a specific exemplary embodiment thereof with reference to the accompanying drawings, wherein.

PREFERRED EMBODIMENT OF THE INVENTION

Figure 1:
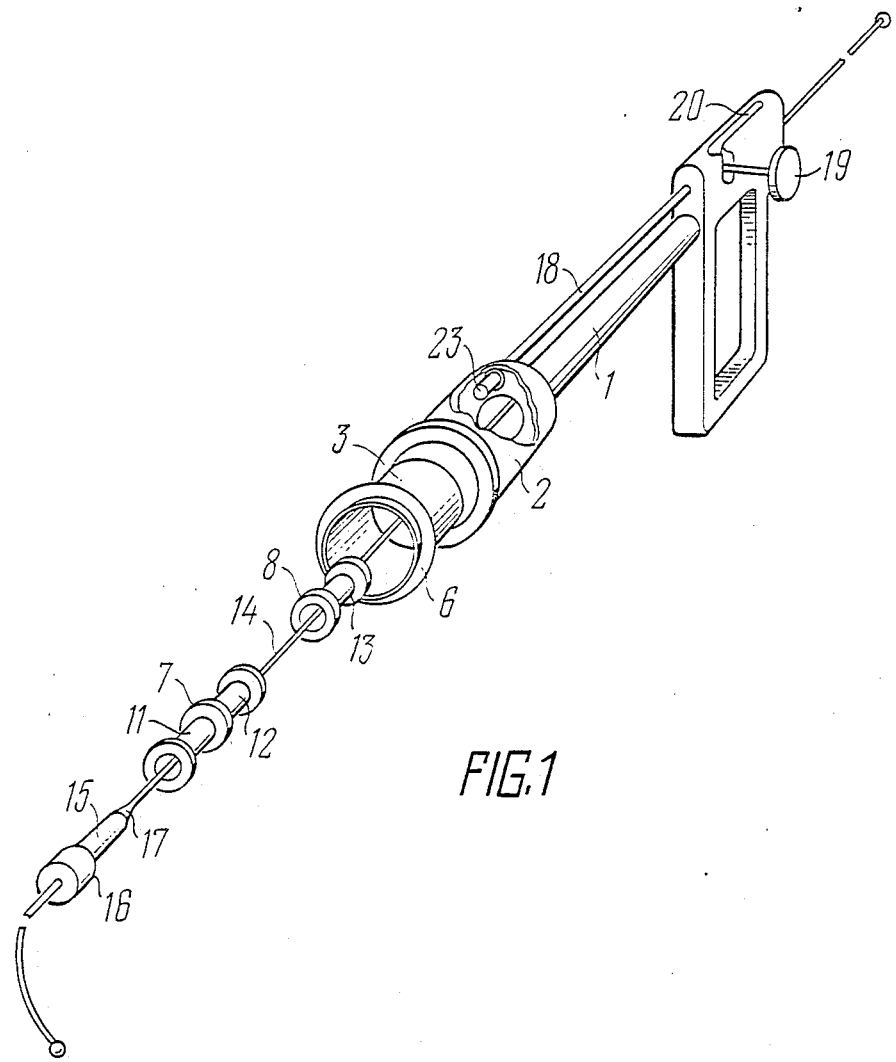
FIG. 1 is a general diagrammatic view of a device for establishing a esophagoenterostomy, according to the invention.
Figure 2:
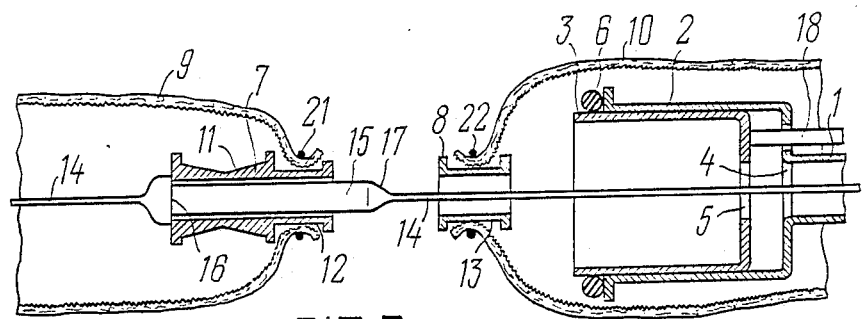
FIG. 2 is a longitudinal sectional view of an anastomosis formation unit.

The device for establishing esophagoenterostomies comprises a hollow housing 1 (FIG. 1), an outer sleeve 2 and an inner sleeve 3, both being interconnected telescopically. The bottom of each of the sleeves 2 and 3 have respective openings 4 and 5 (FIG. 2) through which the interior spaces of the sleeves 2, 3 communicate with the interior space of the housing 1 connected to the sleeve 2. An elastic ring 6 (FIG. 1) is situated on the outside surface of the sleeve 3, for which purpose the inner sleeve 3 is somewhat extended from the outer sleeve 2, whereby an area is formed on the outside surface of the sleeve 3 to mount the elastic ring 6 till anastomosis formation.

The device comprises also bushings 7, 8 (FIGS. 1, 2) on which are secured to the ends of organs 9 and 10 being anastomosed, e.g., esophagus (9) and intestine (10).

The bushing 7 has two protions provided with respective annular grooves 11 and 12 of which the groove 12 serves for fixing the organ 9 being anastomosed, using e.g., a purse-string suture or a ligature. The groove 11 is adapted for anastomosis formation by means of the elastic ring 6. The bushing 8 has one annular groove 13 for fixing the organ 10 being anastomosed in a way similar to that of the organ 9.

A probe 14 shaped as a flexible pullrod is passed through the interior spaces of the bushings 7, 8, the sleeves 2, 3, and the housing 1. The probe 14 has a thickened portion 15 located in the zone of the bushings 7, 8. The diameter of the thickened portion 15 is comparable with the inside diameter of the bushings 7, 8 in order to retain coaxial arrangement of the bushings 7, 8 and hence coaxial arrangement of the organs 9, 10 being anastomosed. The probe 14 has a shoulder 16 on which rests the end of the bushing 7, and a tapered portion 17 for more convenient passing of the probe 14 through the interior of the bushings 7, 8.

The hollow housing 1 carries an adjustable stop 18 shaped as a rod with a bayonet lock 19 located in a slot 20.

The device of the invention operates as follows.

The bushing 7 with the probe 14 preliminarily fitted therein is inserted into the resected end of the organ 9 (i.e., the esophagus) in such a manner that the cylindrical (thickened) portion 15 of the probe enters the bushing 7, whereupon the probe end past the shoulder 16 is guided through the esophagus into the oral cavity, and the esophageal end is fixed by the ligature 21 in the groove 12 of the bushing 7. Then the bushing 8 provided with the groove 13 is introduced into the end of the other organ 10 (i.e. the intestine) to be anastomosed, and the organ 10 is fixed on the bushing 8 with the ligature 22.

Next the device in the assembled state is inserted into the intestine through an additional incision made therein until it contacts the bushing 8 secured in the intestine. The other end of the probe 14 (FIG. 2) is passed through the bushing 8 and then through the entire device till it comes outwards.

Figure 3:
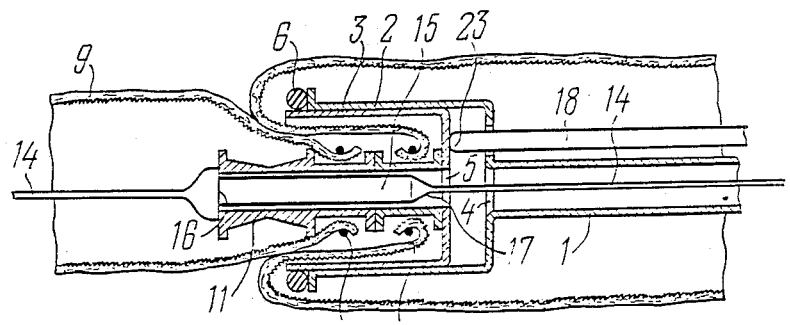
FIG. 3 is a longitudinal sectional view of the unit of FIG. 2 shown at the instant preceding the throwing-off of an elastic ring.

Thereupon one should move the probe 14 with the result that the bushings 7 and 8 are brought in a tight contact with each other and integrated into a single unit, the fixed organ 10 is plunged into the inner sleeve 3, while the organ 9 is invaginated into the organ 10. Then the probe 14 is displaced as far as the bushing 8 thrusts against the bottom of the inner sleeve 3 (FIG. 3).

Any possibility of getting the tissues of the organs 9 and 10 in between the bushings 7, 8 or between the bushing 8 and the bottom of the inner sleeve 3 is precluded, that is, a predetermined position of the groove 11 in the bushing 7 with respect to the elastic ring 6 is assured.

Figure 4:
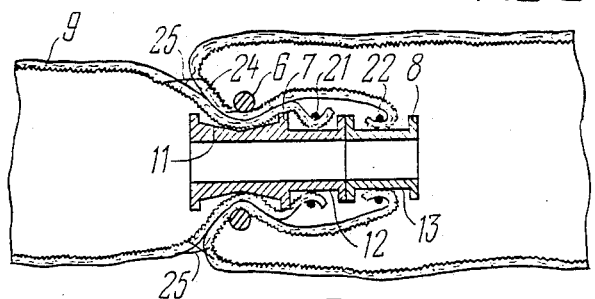
FIG. 4 is a longitudinal sectional view of the unit of FIG. 2 shown after anastomosis formation.

Then the end 23 of the stop 18 is brought out of the interior of the outer sleeve 2 using the bayonet lock 19 and, while further pulling at the probe 14, the inner sleeve 3 together with the bushings 7, 8 is made to travel till thrusting against the bottom of the outer sleeve 2, with the result that the elastic ring 6 runs against the surface of the inner sleeve 3 and gets precisely into the groove 11 (FIG. 4), thus compressing the intestinal walls on the side of its lumen and the walls of the esophagus invaginated into the intestine.

Since the inner sleeve 3 is shorter than the outer sleeve 2 the esophagus is additionally invaginated into the infundibuliform fold 24 of the intestinal wall, thus making it possible to increase the inosculation area of the walls of the esophagus and the intestine being anastomosed, as well as to fix said walls by means of interrupted sutures 25 passing through the superficial layers of the esophageal and intestinal walls.

Then the device is withdrawn from the intestine through the additional incision therein which is then stitched up, while the probe is taken out through the mouth. In this case the internal openings of the bushings 7 and 8 remain open, which provides normal alimentation of the patient, as well as a free discharge of the esophageal content by the natural pathway. In 7 to 10 days the necrotic intestinal and esophageal tissues compressed by the elastic ring 6 are rejected together with the bushings 7, 8 and the elastic ring 6 and brought out by the natural way of elimination.

A total of five surgical procedures for enterostomy have been performed on experimental dogs, all of said procedures being a success; no adverse complications have ensued. There have also been carried out surgeries for gastroectomy in four patients, involving formation of an esophagoenterostomy with the aid of the device considered herein. The anastomosis has been formed for an eight-day period, whereupon the bushings 7, 8 and the elastic ring 6 have been rejected, and the thus-formed suture has been stretched out spontaneously so as to suit the esophagus size. No complications whatever have occurred.

Since inosculation of the walls of a well stretched-out intestine with the esophageal walls occurs under aseptic conditions the thus-established anastomosis is reliable, easily extensible and is practically free from cicatricial tissue.

INDUSTRIAL APPLICABILITY

The invention is applicable in surgery for gastroectomy and in some other operative procedures involving formation of anastomoses on the organs of the digestive tract.

What is claimed is:

1. A device for establishing esophagoenterostomies, comprising a hollow housing (1), an outer sleeve (2) and an inner sleeve (3) interconnected telescopically and communicating with the hollow housing, the inner sleeve (3) being extended from the outer one (2) to form an area adapted to mount an elastic ring (6), which compresses the biological tissues being joined together during anastomosis formation, each of said sleeves having an opening (4, 5) in the bottom thereof, through which the respective sleeve (2, 3) communicated with the hollow housing (1), a bushing (7) accommodated in one of the organs (9) to be anastomosed and having a first annular groove (11) on its outside surface for anastomosis formation by means of the elastic ring (6), and a probe (14) connected to the bushing (7) and passing through the interior spaces of the bushing (7), sleeves (2, 3) and hollow housing (1), characterized in that it incorporates a second bushing (8) having an annular groove (13) on its outside surface for securing thereon the end of the other organ (10) being anastomosed, while the first bushing (7) has a second annular groove (12) on its outside surface, adapted to secure the end of the first organ (9) being anastomosed, said first bushing resting upon a shoulder (16) made in the probe (14), which makes it possible, during anastomosis formation, to join the bushings (7, 8) together into a single unit, to put them inside the sleeves (2, 3) and, while moving the inner sleeve (3), to throw the elastic ring (6) off from the outside surface of the inner sleeve (3) in order to compress the organs (9, 10) being anastomosed in the first annular groove (11) of the first bushing (7), all the motions mentioned above being actuated by virtue of the probe travel.

2. A device as claimed in claim 1, characterized in that the portion of the probe (14) accommodated inside the first bushing (7) and the second bushing (8) has a diameter comparable with the inside diameters of the bushings (7, 8).

3. A device as claimed in claim 1, characterized in that an adjustable stop (18) is provided on the hollow housing (1) is order to fix the inner sleeve (3) in position before anastomosis formation.

* * * * *